(12) United States Patent
Murakami et al.

(10) Patent No.: US 11,432,842 B2
(45) Date of Patent: Sep. 6, 2022

(54) CANNULA

(71) Applicant: MANI, Inc., Utsunomiya (JP)

(72) Inventors: Etsuo Murakami, Utsunomiya (JP); Masanori Oshino, Utsunomiya (JP)

(73) Assignee: MANI, INC., Utsunomiya (JP)

(*) Notice: Subject to any disclaimer, the term of this patent is extended or adjusted under 35 U.S.C. 154(b) by 840 days.

(21) Appl. No.: 16/071,082

(22) PCT Filed: Jan. 18, 2017

(86) PCT No.: PCT/JP2017/001593
§ 371 (c)(1),
(2) Date: Jul. 19, 2018

(87) PCT Pub. No.: WO2017/126565
PCT Pub. Date: Jul. 27, 2017

(65) Prior Publication Data
US 2021/0204972 A1    Jul. 8, 2021

(30) Foreign Application Priority Data
Jan. 19, 2016  (JP) .............................. JP2016-007738

(51) Int. Cl.
*A61B 17/34* (2006.01)
*A61B 17/00* (2006.01)

(52) U.S. Cl.
CPC .... *A61B 17/3421* (2013.01); *A61B 17/00234* (2013.01); *A61B 17/3462* (2013.01); *A61B 2017/00238* (2013.01)

(58) Field of Classification Search
CPC ............ A61B 17/3421; A61B 17/3423; A61B 17/3462; A61B 2017/3419; A61M 39/06;
(Continued)

(56) References Cited

U.S. PATENT DOCUMENTS

| | | | |
|---|---|---|---|
| 4,809,679 A * | 3/1989 | Shimonaka | A61B 1/00137 600/154 |
| 6,416,499 B2 * | 7/2002 | Paul, Jr. | A61M 39/0606 604/167.04 |
| 2008/0161845 A1 | 7/2008 | Murakami et al. | |

FOREIGN PATENT DOCUMENTS

| JP | H0357202 Y2 | 12/1991 |
|---|---|---|
| JP | 2008142533 A | 6/2008 |
| WO | 2010126076 A1 | 11/2010 |

OTHER PUBLICATIONS

International Search Report (ISR) for Application No. PCT/JP2017/001593 dated Mar. 28, 2017.

(Continued)

*Primary Examiner* — Diane D Yabut
(74) *Attorney, Agent, or Firm* — Isshiki & Partners; Joseph P. Farrar

(57) ABSTRACT

There is provided a cannula that suppresses leakage of vitreous humor, etc., from a slit through which a surgical tool is inserted. A cannula (10) used for piercing through an eyeball during an ophthalmic operation, includes: a pipe (11); a cylindrical base (12) fitted together with the circumference of a base end of the pipe (11); a resin cap (13) including a cover surface (13c) covering the surface of the base end of the pipe (11) and a side surface (13a) covering a cylindrical side surface of the base (12); and a slit (13d) passing through the center of the cover surface (13c). The outer diameter of the cylindrical side surface of the base (12) at a position where the cylindrical side surface of the base (12) touches the side surface (13a) of the cap is larger than the inner diameter of the side surface of the cap.

2 Claims, 4 Drawing Sheets

(58) Field of Classification Search
CPC ........ A61M 203/064; A61M 203/2426; A61M 2039/064; A61M 2039/2426; A61M 39/0606; A61M 39/0613; A61M 2039/0072; A61M 2039/0633
USPC .................................................... 604/167.04
See application file for complete search history.

(56) References Cited

OTHER PUBLICATIONS

Translation of the ISR for Application No. PCT/JP2017/001593 dated Mar. 28, 2017.
Written Opinion of the International Search Authority for Application No. PCT/JP2017/001593 dated Mar. 28, 2017.

* cited by examiner

CANNULA

CROSS-REFERENCE TO RELATED APPLICATIONS

The present application is a national phase entry under 35 U.S.C. § 371 of International Application No. PCT/JP2017/001593, filed Jan. 18, 2017, which in turn claims priority from Japanese Patent Application No. 2016-007738 filed Jan. 19, 2016, the entire disclosures of which are hereby incorporated by reference herein.

TECHNICAL FIELD

The present invention relates to a cannula used in ophthalmic operations.

BACKGROUND ART

The cannula is used when using a surgical tool or the like within an eyeball during an ophthalmic operation (e.g., Patent Document 1). FIG. 5 is a cross-section of a conventional cannula, and FIG. 6 is a diagram illustrating a state of an ophthalmic operation. A conventional cannula 110 is configured by fitting a metal pipe 111 into a base 112 made of resin, and covering and enveloping a cylindrical side surface of the base 112 and the base end of the pipe 111 by a cap 113 made of silicone rubber.

The base 112 has a function of a stopper by touching the surface of an eyeball A when the pipe 111 is pierced in, and the cap 113 has a function of controlling leakage of vitreous humor, etc., from the inside of the eyeball A. The base 112 has a nearly cylindrical shape and a groove 112a formed along the circumference near the middle position of its side surface. The groove 112a is used to hold the cannula 110 with tweezers, and to fit in a locking part 113b of the cap 113 when covering the base 112 with the cap 113.

The cap 113 has a nearly cylindrical shape with one end closed by a cover surface 113c, and has a convex locking part 113b, which is provided on an end part of a side surface 113a and faces the center of the circle. A slit 113d, which passes through the inside of the pipe 111 from the outside of the cap 113, is provided near the center of the cover surface 113c, and various surgical tools 20, optical instruments for monitoring, etc., may then be inserted in the eyeball A through the slit 113d.

PRIOR ART DOCUMENTS

Patent Documents

[Patent Document 1] WO 2010/126076A

DISCLOSURE OF INVENTION

Problem to be Solved by the Invention

However, with the conventional cannula, there are cases where vitreous humor, etc., may leak from the slit formed in the cap particularly when an inserted surgical tool is moved, etc.

In light of this problem, the present invention aims to provide a cannula that can further suppress leakage of vitreous humor, etc., from the slit through which a surgical tool is inserted.

Solution to the Problem

The cannula according to the present invention is used for piercing through an eyeball during an ophthalmic operation. The cannula includes: a pipe; a cylindrical base fitted together with the circumference of a base end of the pipe; a resin cap comprising a cover surface covering the surface of the base end of the pipe and a side surface covering a cylindrical side surface of the base; and a slit passing through the center of the cover surface. The outer diameter of the cylindrical side surface of the base at a position where the cylindrical side surface of the base touches the side surface of the cap is greater than the inner diameter of the side surface of the cap.

A structure where the base includes a groove along the circumference of the cylindrical side surface, the cap comprises a locking part fitted together with the groove so as to touch a groove bottom surface of the groove, the outer diameter of the cylindrical side surface of the base is outer diameter of the groove bottom surface, and the inner diameter of the side surface of the cap is inner diameter of the locking part may be adopted.

Furthermore, it is favorable if the slit is linear, and the outer diameter of the cylindrical side surface of the base orthogonal to the slit is larger than the inner diameter of the side surface of the cap.

Advantageous Effect of the Invention

According to the present invention, there is a beneficial effect that since a force acting toward the center of the cap is generated with the cap covering the base, a force is applied in the closing direction of the slit so as to effectively suppress leakage of vitreous humor, etc.

DESCRIPTION OF EMBODIMENTS

An embodiment according to the present invention is described below with reference to accompanying drawings.

Figure 1:
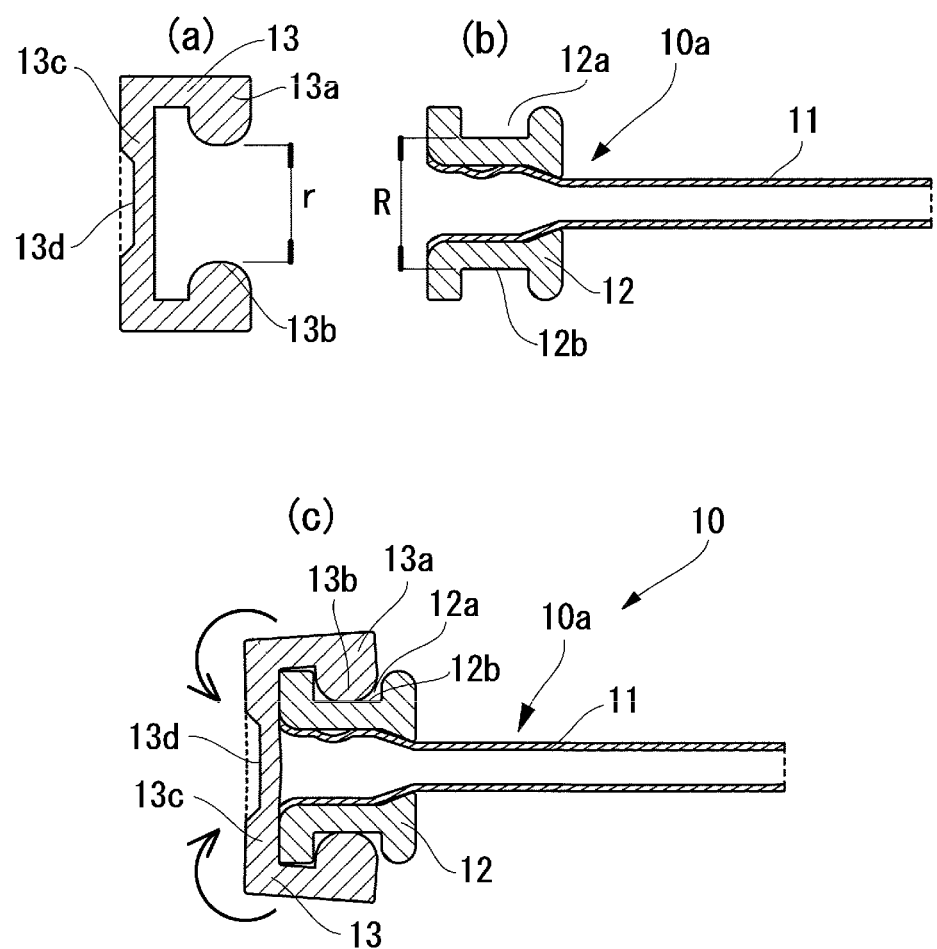
FIG. 1 shows cross-sections of (a) a cap and (b) a main body part used for a cannula of the present invention, respectively, and (c) is a cross-section of the entire cannula.
Figure 2:
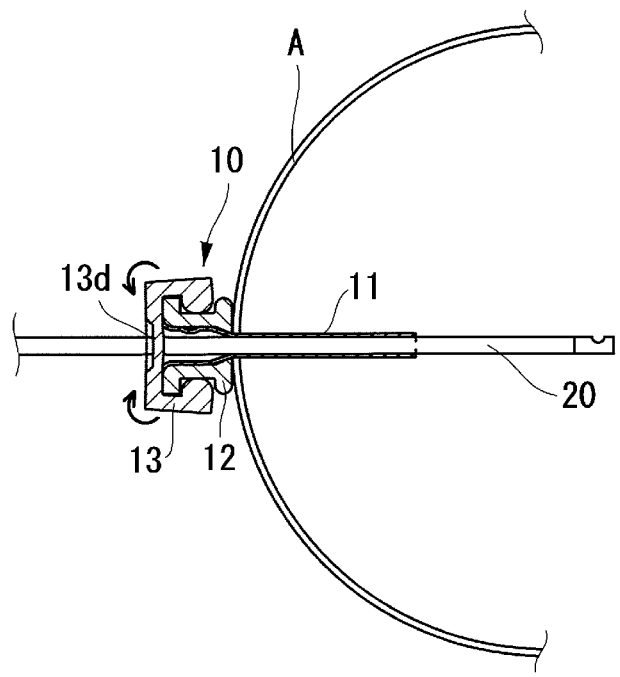
FIG. 2 is a diagram describing a usage of the cannula of the present invention.

FIG. 1 shows cross-sections of (a) a cap and (b) a main body part used for a cannula of the present invention, respectively, and (c) is a cross-section of the entire cannula. FIG. 2 is a diagram describing a usage of the cannula of the present invention. The configuration of a cannula 10 of the present invention includes a main body part 10a made up of a metal pipe 11 and a resin base 12 having a nearly cylindrical shape, and cap 13 made of silicone rubber.

Here, the pipe 11 is a portion that pierces into an eyeball A, the base 12 has a function of a stopper by touching the surface of the eyeball A when the pipe 11 is pierced in, and the cap 13 is for preventing leakage of vitreous humor, etc., from the inside of the eyeball A. At the time of use, a surgical tool 20 such as a vitreous body cutter is inserted from a slit 13d formed in a cover surface 13c of the cap 13 so as to perform surgery on the inside of the eyeball A. Note that while the pipe is preferably made of metal, the material thereof is not limited, and resin, etc., may be used.

The cannula 10 has a structure in which the base 12 and a base end of the pipe 11 are fitted together to form the main body part 10a, as with the conventional cannula, and a cylindrical side surface of the base 12 and the surface of the base end of the pipe 11 are covered and enveloped by a cap 13 made of silicone rubber, resulting in a state where an opening in the base end surface of the pipe 11 is covered by the cover surface 13c of the cap 13. Note that while the cap 13 is preferably made of silicone rubber, other resins may also be used.

Shapes of the base 12 and the cap 13 are also generally the same as the conventional cannula, wherein the base 12 has a nearly cylindrical shape and a groove 12a formed along the circumference near the middle position of its side surface. The cap 13 has a nearly cylindrical shape with one end covered by a cover surface 13c, and has a convex locking part 13b provided on an end part of a side surface 13a facing the center of the circle.

The locking part 13b is fit into the groove 12a when attaching the cap 13 on the base 12. At this time, a front end of the locking part 13b fitted into the groove 12a touches a groove bottom surface 12b of the groove 12a. In the example shown in FIG. 1, outer radius R of the groove bottom surface 12b is larger than inner radius r of the locking part 13b, thereby allowing a structure in which the front end of the locking part 13b completely touches the groove bottom surface 12b. More specifically, when the cap 13 is conventional one and the depth of the groove 12a of the base 12 is shallower than that of the conventional one, or conversely, when the base 12 is conventional one and the convex shape of the locking part 13b of the cap 13 is larger than that of the conventional one, the front end of the locking part 13b and the groove bottom surface 12b can be contacted.

In the case of the above-given structure, since the side surface 13a of the cap 13 opens outward due to contact between the groove bottom surface 12b on the cylindrical side surface of the base 12 and the locking part 13b on the side surface 13a of the cap 13, the cap 13 is deformed in directions indicated by arrows in (c) of FIG. 1 and FIG. 2, thereby generating a force acting toward the center of the cover surface 13c. That is, since a slit 13d that passes through to the inner side of the pipe 11 from the outside of the cap 13 is opened near the center of the cover surface 13c, a force acts in the closing direction of the slit 13d. As a result, it is natural that vitreous humor, etc., does not easily leak out when the surgical tool 20 such as a vitreous body cutter is not inserted into the slit 13d, and even when various surgical tools 20 inserted through the slit 13d are moved, gaps do not easily become larger between the slit 13d and the surgical tools 20, thereby further suppressing leakage of vitreous humor, etc., to the outside.

Figure 3:
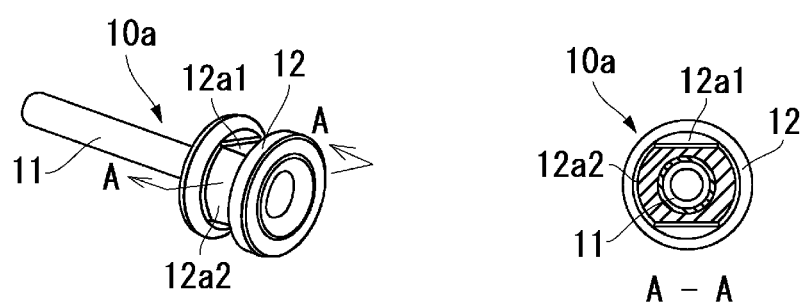
FIG. 3 shows an oblique view of the cannula main body part, and a cross-section cut along a line A-A of a base portion.
Figure 4:
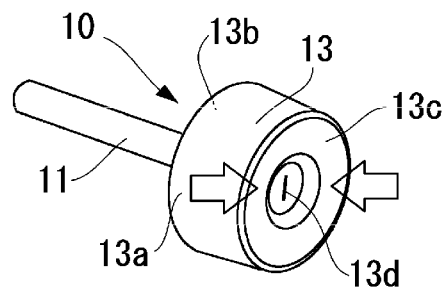
FIG. 4 is an oblique view of the cannula to which a force is applied only in a closing direction of the slit.
Figure 5:
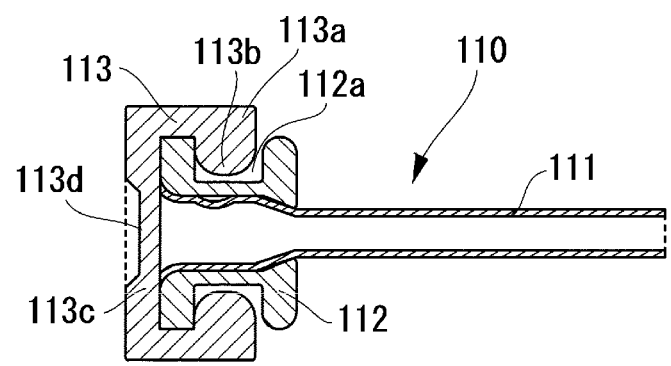
FIG. 5 is a cross-section of a conventional cannula.
Figure 6:
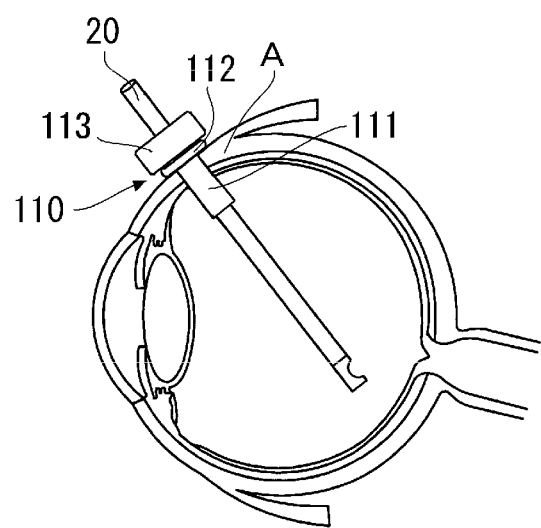
FIG. 6 is diagram illustrating a state of an ophthalmic operation.

Moreover, a working example of devising a groove shape in the base in accordance with the orientation of the slit in order to further effectively prevent leakage of vitreous humor, etc., is described. FIG. 3 shows an oblique view of the cannula main body part, and a cross-section cut along a line A-A of a base portion. FIG. 4 is an oblique view of the cannula to which a force is applied only in the closing direction of the slit.

Since the slit 13d is typically linear, it is effective to apply a force orthogonally to the length of the slit as shown in FIG. 4 in order to prevent leakage from the slit 13d. Therefore, a deep groove 12a1 and a shallow groove 12a2 are provided to the groove 12a of the base 12. In the example of FIG. 3, upper and lower portions of the base 12 are the deep groove 12a1, and left and right portions are the shallow groove 12a2. More specifically, the shallow groove 12a2 in the left and right portions has an arc shape, and the deep groove 12a1 in the upper and lower portions has a bow shape resulting from linearly cutting out an arc. Note that the shape of the groove 12a is not limited to an arc or straight line as mentioned, but may have a structure in which a depression or a projection is formed in the groove 12a, for example.

The cap 13 covers the base 12 such that the linear direction of the slit 13d is in the up and down direction of such a main body part 10a. As a result, in FIG. 4, since forces act on the cover surface 13c strongly from the left and right, forces are applied in the closing direction of the slit 13d (orthogonal to the slit). Note that the groove thickness may be set according to various conditions such as length of the slit 13d such that forces do not act at all or act weaker than those in the orthogonal direction.

While the example of FIG. 3 illustrates the case where the groove depth of the base 12 is varied, similar results may be obtained even by making the groove thickness of the base 12 constant and varying height of the locking part 13b of the cap 13 fitted into the groove. That is, by making the height of the locking part 13b at a position orthogonal to the length of the slit 13d higher than other positions, it is possible to apply force in the closing direction of the slit 13d, as illustrated in FIG. 4.

As described above, the cannula of the present invention may suppress leakage of vitreous humor, etc., effectively since a force acting toward the center of the cap is generated when the cap is covering the base and a force is then applied in the closing direction of the slit.

EXPLANATION OF REFERENCES

10: Cannula
11: Pipe
12: Base
12a: Groove
12a1: Deep groove
12a2: Shallow groove
12b: Groove bottom surface
13: Cap
13a: Cap side surface
13b: Locking part
13c: Cover surface
13d: Slit
20: Surgical tool
A: Eyeball

The invention claimed is:

1. A cannula for piercing an eyeball during an ophthalmic operation, comprising:
   a pipe;
   a cylindrical base fitted together with a circumference of a base end of the pipe;
   a resin cap comprising a cover surface covering a surface of the base end of the pipe and a side surface covering a cylindrical side surface of the base; and
   a slit passing through a center of the cover surface, wherein
   an outer diameter of the cylindrical side surface of the base at a position where the cylindrical side surface of the base touches the side surface of the cap is larger than an inner diameter of the side surface of the cap, the slit is linear, the outer diameter of the cylindrical side surface of the base orthogonal to the slit is larger than the inner diameter of the side surface of the cap, and the outer diameter of the cylindrical side surface of the base orthogonal to the slit is larger than the outer diameter of the cylindrical side surface of the base parallel to a length of the slit.

2. The cannula of claim 1, wherein the base comprises a groove along a circumference of the cylindrical side surface, the cap comprises a locking part fitted together with the groove so as to touch a groove bottom surface of the groove, the outer diameter of the cylindrical side surface of the base is an outer diameter of the groove bottom surface, and the inner diameter of the side surface of the cap is an inner diameter of the locking part.

\* \* \* \* \*